(12) United States Patent
Bal

(10) Patent No.: US 9,076,222 B2
(45) Date of Patent: Jul. 7, 2015

(54) USE OF COLLECTION OF PLANS TO DEVELOP NEW OPTIMIZATION OBJECTIVES

(75) Inventor: Matthieu Bal, Cadier en Keer (NL)

(73) Assignee: Koninklijke Philips N.V., Eindhoven (NL)

( * ) Notice: Subject to any disclaimer, the term of this patent is extended or adjusted under 35 U.S.C. 154(b) by 407 days.

(21) Appl. No.: 13/511,670

(22) PCT Filed: Nov. 18, 2010

(86) PCT No.: PCT/IB2010/055268
§ 371 (c)(1),
(2), (4) Date: May 24, 2012

(87) PCT Pub. No.: WO2011/073820
PCT Pub. Date: Jun. 23, 2011

(65) Prior Publication Data
US 2012/0280135 A1    Nov. 8, 2012

Related U.S. Application Data

(60) Provisional application No. 61/286,860, filed on Dec. 16, 2009.

(51) Int. Cl.
*A61B 6/00*    (2006.01)
*A61N 5/10*    (2006.01)
(Continued)

(52) U.S. Cl.
CPC ............... *G06T 7/0083* (2013.01); *A61B 6/52* (2013.01); *A61B 5/004* (2013.01); *A61B 5/0033* (2013.01);
(Continued)

(58) Field of Classification Search
CPC ........ A61B 5/00; A61B 5/0033; A61B 5/004; A61B 5/103; A61B 5/107; A61B 5/4836; A61B 6/00; A61B 6/50; A61B 6/52; A61B 6/5211; A61B 6/5229; A61B 6/5235; A61B 6/5241; A61B 6/5247; A61B 5/5294; A61N 5/00; A61N 5/10; A61N 5/103; A61N 5/1031; A61N 5/1036; A61N 5/1037; A61N 5/1038; A61N 5/1039; A61N 5/1042; A61N 5/1048
USPC ............ 378/65, 162, 165, 210, 901; 382/128, 382/131, 173, 174, 256, 282, 283, 308, 325
See application file for complete search history.

(56) References Cited

U.S. PATENT DOCUMENTS

| 7,421,122 | B2 | 9/2008 | Kaus et al. | |
| 2006/0110037 | A1* | 5/2006 | Kaus et al. | ..................... 382/173 |

(Continued)

FOREIGN PATENT DOCUMENTS

WO    2009095837 A2    8/2009

OTHER PUBLICATIONS

Brock, K. K., et al.; Feasibility of a Novel Deformable Image Registration Technique to Facilitate Classification, Targeting, and Monitoring of Tumor and Normal Tissue; 2006; Int. J. Radiation Oncology Biol. Phys.; 64(4)1245-1254.

(Continued)

*Primary Examiner* — Anastasia Midkiff

(57) ABSTRACT

A radiation therapy system includes a diagnostic image scanner (12) which acquires a multidimensional dataset of a subject that is reconstructed into at least one image representation of an object of interest. An image processing apparatus (72), of radiation therapy system, includes a segmentation unit (74) which identifies a surface contour of the object of interest, or other critical structures. A masking unit (82) determines a non-constant margin, based on the identified surface contour and appends the determined non-constant margin to the identified surface contour. The non-constant margin is based on at least one of anisotropic motion, surface morphology, positional uncertainty, proximity to other organs, and probability of dose distribution. A planning processor (70) generates a radiation therapy plan which limits the delivery of therapeutic radiation to anatomy associated with the surface contour and appended non-constant margin. A radiation delivery system (40) delivers therapeutic radiation according to the generated plan.

12 Claims, 3 Drawing Sheets

(51) Int. Cl.
*G06T 7/00* (2006.01)
*A61B 5/00* (2006.01)

(52) U.S. Cl.
CPC .............. *A61N 5/1039* (2013.01); *A61N 5/103* (2013.01); *A61B 6/5229* (2013.01); *A61B 6/5211* (2013.01); *G06T 2207/10072* (2013.01); *G06T 2207/30096* (2013.01)

(56) References Cited

U.S. PATENT DOCUMENTS

| | | | |
|---|---|---|---|
| 2006/0210158 A1* | 9/2006 | Pekar et al. | 382/173 |
| 2007/0211939 A1* | 9/2007 | Kaus et al. | 382/173 |
| 2008/0123927 A1* | 5/2008 | Miga et al. | 382/131 |
| 2008/0177179 A1 | 7/2008 | Stubbs et al. | |
| 2009/0226060 A1* | 9/2009 | Gering et al. | 382/128 |
| 2009/0324078 A1* | 12/2009 | Wu et al. | 382/173 |
| 2010/0183121 A1* | 7/2010 | Riker et al. | 378/65 |

OTHER PUBLICATIONS

Foskey, M., et al.; Large deformation three-dimensional image registration in image-guided radiation therapy; 2005; Phys. Med. Biol.; 50:5869-5892.

Hysing, L. B., et al.; Planning Organ at Risk Volume Margins for Organ Motion of the Intestine; 2006; Radiotherapy & Oncology; 80(3)abstract.

McBain, C. A., et al.; Radiation Therapy for Muscle-Invasive Bladder Cancer: Treatment Planning and Delivery in the 21st Century; 2005; Seminars in Radiation Oncology; 15(1)42-48.

Meijer, G. J., et al.; What CTV-to-PTV Margins Should be Applied for Prostate Irradiation? Four-dimensional Quantitative Assessment Using Model-Based Deformable Image Registration Techniques; 2008; Int. J. Radiation Oncolocy Biol. Phys.; 72(5)1416-1425.

Pekar, V., et al.; Automated model-based organ delineation for radiotherapy planning in prostatic region; 2004; Int. J. of Radiation Oncology Biology Physics; 60(3)abstract.

Nishimura, Y.; Intensity modulated radiation therapy for head and neck cancer (IMRT); 2008; Journal of Clinical Oncology; 227(9)704-709.

Mangar, S. A., et al.; Evaluating Inter-fractional Changes in Volume and Position during Bladder Radiotherapy and the Effect of Volume Limitation as a Method of Reducing the Internal Margin of the Planning Target Volume; 2008; Clinical Oncology; pp. 1-7.

Meijer, G. J., et al.; Three-dimensional analysis of delineation errors, setup errors, and organ motion during radiotherapy of bladder cancer; 2003; International Journal of Radiation Oncology Biology Physics; 55(5)1277-1287.

* cited by examiner

USE OF COLLECTION OF PLANS TO DEVELOP NEW OPTIMIZATION OBJECTIVES

CROSS REFERENCE TO RELATED APPLICATIONS

This application claims the benefit of U.S. provisional application Ser. No. 61/286,860 filed Dec. 16, 2009, which is incorporated herein by reference.

The present application relates to methods and systems for radiation therapy planning. It finds particular application to identifying anatomical features in medical images and delivering radiation therapy thereto.

Radiation therapy is a common therapeutic technique in oncology in which a dose of high energy gamma (γ) radiation, particle beam, or other radiation is delivered to a patient's body to achieve a therapeutic effect, i.e. eradicate cancerous tissue. A plurality of tomographic radiation beams, or a single radiation beam, is intensity-modulated using multi-leaved collimators or other beam shaping elements to precisely irradiate the target volume, e.g. cancerous tissue, while limiting exposure of sensitive nearby organs at risk. The radiation therapy session(s) are planned prior to radiation treatment based on one or more planning volumetric images, e.g. a computed tomography (CT) image or the like, of the tumor and surrounding tissue. A computerized planning system automatically or semi-automatically segments the boundaries of the target volume and the healthy surrounding tissue, some of which are sensitive, at risk organs that are to be avoided by the radiation beam. Using the boundary information, the planning system optimizes the intensity modulation parameters to deliver the radiation primarily within the contours corresponding to the cancerous volumes while limiting exposure within the contours corresponding to the organs at risk. To ensure that the target is fully irradiated, a fixed margin is defined around the determined contour of the target volume to account for uncertainties such as organ motion and patient position. Namely, the target is enlarged by a fixed margin in all directions to improve the probability that the target is actually irradiated. Relying on a fixed margin of uncertainty may lead to inadequate irradiation of the cancer, unnecessary irradiation damage of surrounding tissue, or both.

For example, in prostate cancer treatment planning, the prostate is contoured and identified as the target volume while organs such as the bladder, rectum, femur heads, and so forth are contoured and identified as organs at risk whose radiation exposure is to be limited. Because these organs are in such close proximity, the usual approach of adding a fixed margin to the target volume poses a risk to these sensitive organs. Not adding the margin poses a risk that the cancer will not be completely eradicated.

The present application provides a new and improved method and apparatus for radiation therapy planning which overcomes the above-referenced problems and others.

In accordance with one aspect, a method for image segmentation of anatomical features is presented. The method includes identifying a surface contour of at least one object of interest from a multi-dimensional data set and determining a non-constant margin based on the identified surface contour, the non-constant margin being appended to the identified surface contour.

In accordance with one another aspect, a method for radiation therapy is presented. The method includes acquiring a multidimensional dataset of a subject and reconstructing the multidimensional dataset into at least one image representation of at least one anatomical feature of the subject. The image representation is segmented according to the method for image segmentation.

In accordance with one another aspect, a radiation therapy system is presented. The radiation therapy system includes a diagnostic image scan, a radiation delivery system, and a radiation therapy planning processor programmed to perform the method of image segmentation of anatomical features.

In accordance with one another aspect, an image processing apparatus is presented. The image processing apparatus includes a segmentation unit which identifies a surface contour of at least one object of interest from a multi-dimensional data set and a masking unit which determines a non-constant margin based on the identified surface contour and appends the determined non-constant margin to the identified surface contour.

In accordance with one another aspect, a radiation therapy system is presented. The radiation therapy system includes a diagnostic image scanner which acquires a multidimensional dataset of a subject and generates at least one image representation of an object of interest from the multidimensional dataset and the image processing apparatus.

One advantage is that radiation exposure to healthy tissue is reduced.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

Figure 1:
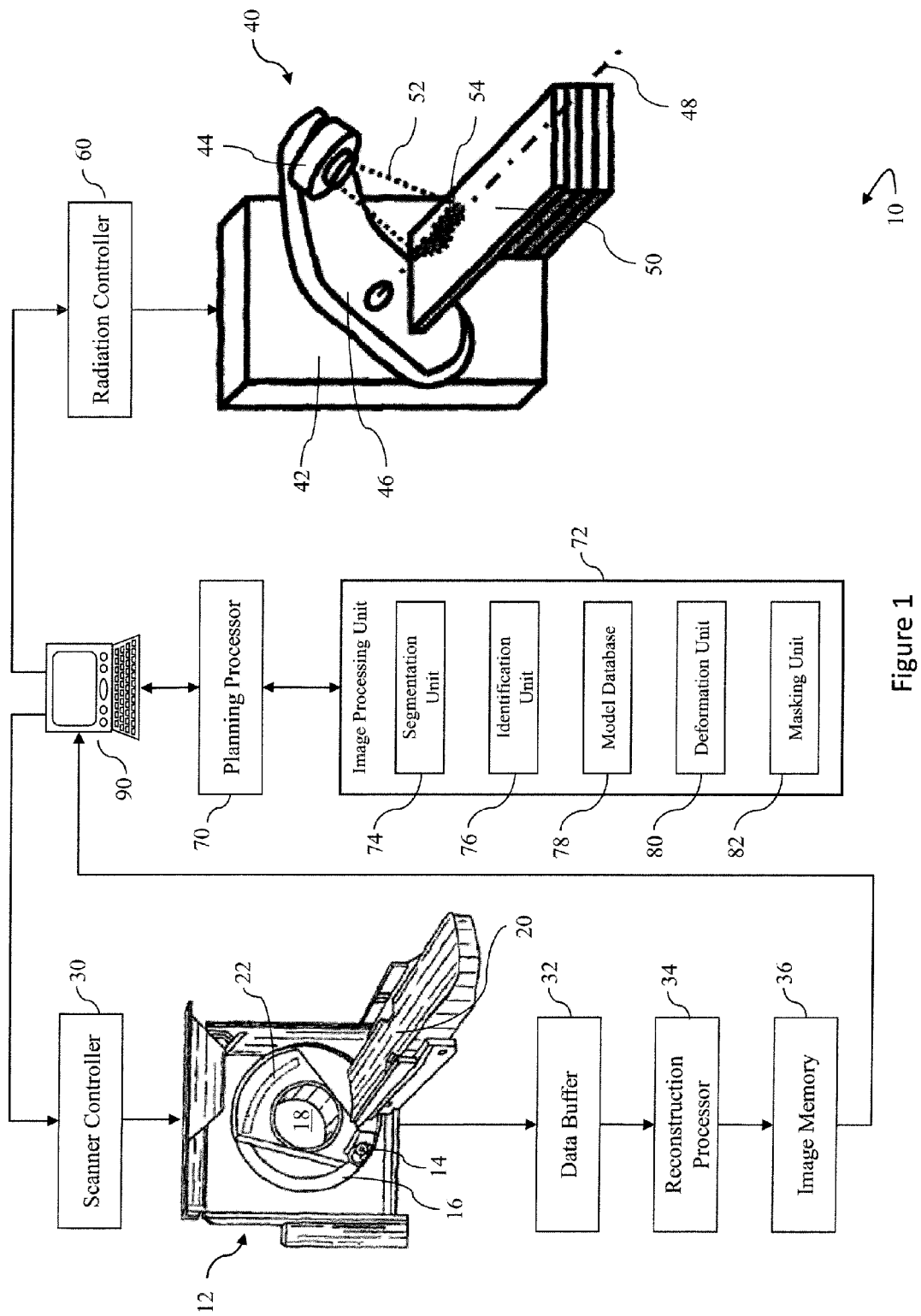
FIG. 1 is a diagrammatic view of a radiation therapy system with an image processing unit to determine a non-constant margin.

With reference to FIG. 1, a therapy system 10, such as a radiation therapy system, includes a diagnostic imaging scanner 12 such as a computed tomography (CT) imaging scanner, an MRI scanner, or the like for obtaining diagnostic images for use in planning the radiation therapy protocol. The CT imaging scanner 12 includes an x-ray source 14 mounted on a rotating gantry 16. The x-ray source 14 produces x-rays passing through an examination region 18, where they interact with a target area of a subject (not shown) supported by a support 20 which positions the target area within the examination region 18. An x-ray detector array 22 is arranged to receive the x-ray beam after it passes through the examination region 18 where the x-rays interact with and are partially absorbed by the subject. The detected x-rays therefore include absorption information relating to the subject.

The CT scanner 12 is operated by a controller 30 to perform selected imaging sequences of a selected target area of the subject which is to be treated by radiotherapy. The imaging sequences acquire a multi-dimensional diagnostic imaging dataset of the target area and adjacent tissue. The diagnostic imaging dataset is stored in a data buffer 32. A reconstruction processor 34 reconstructs 3D image representations from the acquired imaging data, and the reconstructed image representations are stored in a diagnostic image memory 36. Taken together, the CT scanner 12, controller 30, and reconstruction processor 34 define a means for generating a diagnostic image.

The described diagnostic imaging system is exemplary only. Those skilled in the art will recognize that the CT scanner 12 is optionally replaced by other types of diagnostic imaging scanners, such as a magnetic resonance imaging (MRI) scanner, a positron emission tomography (PET) scanner, a single photon emission computed tomography (SPECT) scanner, or the like.

In the illustrated embodiment, the diagnostic imaging apparatus 12 is separate from a therapy delivery system 40, but they can be combined into a single housing. The therapy delivery system can be an external radiotherapy delivery system or an internal radiotherapy delivery system, e.g. brachytherapy. Optionally, markers are applied to the subject prior to the diagnostic imaging, and remain in place for the subsequent radiotherapy to provide registration between the diagnostic images and the radiotherapy delivery. Other methods for spatial registering between diagnostic image acquisition and the radiotherapy are also contemplated, such as using intrinsic anatomical markers. It is also contemplated to integrate the diagnostic imaging scanner with the radiotherapy apparatus to reduce misregistration between the diagnostic imaging and the radiotherapy.

The radiation delivery system 40 includes a radiation delivery apparatus 42 which has a radiation source 44, such as a linear accelerator, focused x-ray, or the like mounted on a rotating gantry 46. The gantry 46 rotates or steps a radiation source 44 about an axis of rotation 48. A support 50 rigidly positions the subject with the target area exposed to an intensity-modulated radiation beam 52 produced by the radiation source 44. The support 50 positions and moves the subject while the gantry 46 rotates the radiation source 44 about the subject. The radiation beam 52 has a cross-sectional area 54 with an adjustable intensity and/or perimeter. The radiation beam 52 can be applied continuously or can be pulsed on and off during therapy. Optionally, a radiation detector system disposed on an opposite side of the patient from the source to monitor intensities of radiation traversing the patient. Data from the detector can be reconstructed into a low resolution projection image to monitor the alignment of the beam and the target and the dose. The radiation delivery system 40 is operated by a radiation controller 60 to perform selected radiation protocol as prescribed by a planning processor 70. Taken together, the radiation delivery system 40, radiation controller 60, and planning processor 70 define a means for delivering radiation therapy.

The planning processor 70, which defines a means for planning radiation therapy, determines a radiation therapy plan based on the acquired diagnostic image representations of the object of interest and critical organs from the imaging apparatus 12. The object of interest may be a cancerous tumor or a lesion that is to receive the radiation therapy from the radiation delivery system 40. The critical structures include healthy or sensitive tissue that must be spared as much as possible or have a higher precedence over non-critical tissue, such as the spinal cord or the like. Typically, once the object of interest is located and identified an isotropic margin is appended to a surface contour of the object of interest to expand the area to be irradiated which increases the probability that the entire object of interest has been irradiated, i.e. the anatomy corresponding to the appended margin will receive the same radiation dose. The margin accounts for motion uncertainty related to motion during treatment session such as pulmonary motion, cardiac motion, etc. or even motion in between treatment sessions such as patient positioning, rectal or bladder filling, or the like. The problem with appending an isotropic margin is that if the object of interest undergoes motion in only one direction or even two directions, the isotropic margin assumes it undergoes motion in all directions equally resulting in unnecessary irradiation of healthy tissue.

With continuing reference to FIG. 1, an image processing unit 72, which communicates with the planning processor 70 and also defines a means for image processing, determines an anisotropic or non-constant margin based on characteristics of the object of interest and/or critical structures, projected motion, and other sources of potential error. The image processing unit includes a segmentation unit 74, which defines a means for segmentation, which autonomously or semi-autonomously delineates the surface contour of the object of interest and the critical structures from the acquired diagnostic image representation. Any one of known segmentation methods such as clustering, feature extraction, model based, or the like are contemplated. An identification unit 76, which define a means for identifying, matches the delineated surface contour to reference data. The reference data includes a database 78 of surface models corresponding to various organs and/or tissue types from which a relevant surface model is matched to the delineated contour of the object of interest. Matching techniques may include maximum-likelihood estimators, neural networks, or the like.

A non-constant margin is associated to each surface model. For example, the surface model includes a plurality of regions, each region has a margin width associate with it. The width of the margin at the individual regions of the surface model can be dependent on a number of factors. Factors include the morphology of the object of interest, e.g. whether the surface is smooth, irregular, having protrusions like tendrils, etc. Uncertainty of boundary position due to motion in one or more directions, e.g. a lung tumor may undergo motion in the coronal direction due to breathing; therefore, the regions of the surface model which are perpendicular to the mean direction of travel have wider associated margins. Physiological function of the tissue to be irradiate or the function of nearby structures, both critical and non-critical, and proximity to critical structures is also considered. Factors may be dependent on the radiation delivery system 40 such as beam width, beam intensity, beam scattering, gantry speed, gantry oscillation or vibration, or the like. In addition to the margin width, each region of the surface model may also have a weight factor corresponding to the intensity of radiation therapy beam delivered to the anatomy corresponding to that region. In one embodiment, the weight factor is constant such that the corresponding margin behaves like a step function. In another embodiment, the weight factor is non-linear such as a gradient function where the beam intensity increases/decreases towards the edge of the margin opposite the object of interest. For example, the weigh factor can also be selected to deliver a radiation pattern that delineates the prescribed dose to edge areas of the target with a selectable certainty, e.g. a 99% probability that the prescribed dose is delivered to all parts of the target, or a 95% probability.

Figure 2:
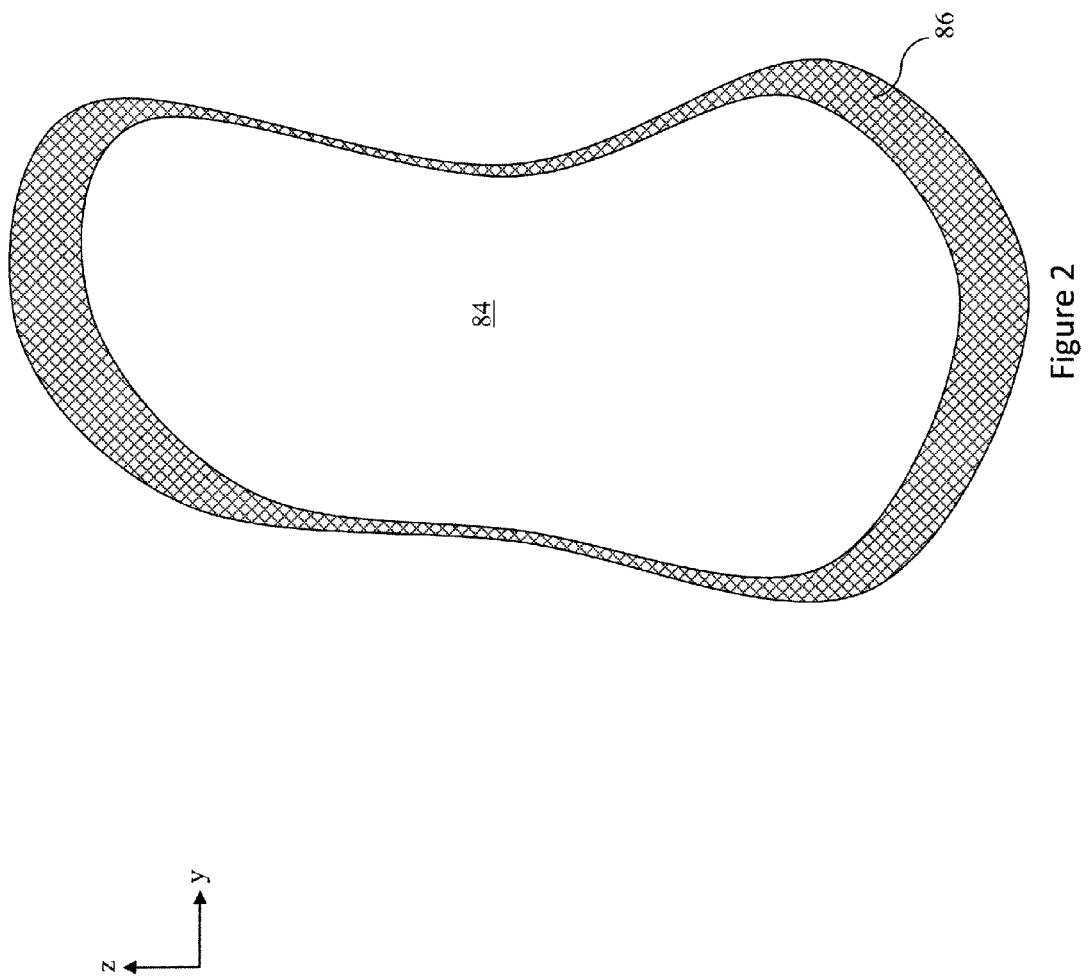
FIG. 2 is a two-dimensional axial slice of an object of interest and an appended non-constant margin.

A deformation unit 80, which defines a means for deforming, adapts a surface of the surface model to correspond to the geometry of the surface contour of the object of interest. A masking unit 82, which defines a means for masking, appends the non-constant margin to the object of interest and the planning processor 70 generates an intensity map based on the appended surface contour of the object of interest and the contours of critical structures. With reference to FIG. 2, an example of an axial 2D slice of the surface model 84 of the object of interest with the appended non-constant margin 86 is illustrated. The net movement of the object of interest is in the z-direction, thus the non-constant margin 86 is wider to account for positional uncertainties of surfaces perpendicular or substantially perpendicular to the direction of travel. Surfaces substantially parallel to the direction of travel, i.e. the y-direction in the illustrated embodiment, have a narrower non-constant margin 86 associated with them. The intensity map maps out therapy beam trajectories, geometries, and/or intensity for the radiation controller to control the radiation delivery system 40. The planning processor outputs the intensity map to a console 90. The console 90 includes a graphic user interface and also includes a user input device which a clinician can use for controlling the scanner controller 30 or radiation controller 60 to select scanning sequences or protocols and treatment schemes or doses respectively according to the generated intensity map. The console displays diagnostic images, segmentation tools, surface models, the non-constant margins, and the like. Taken together, the segmentation unit 74, identification unit 76, database 78, deformation unit 80, and masking unit 82 define a means for generating a non-constant margin.

The console 80 includes a graphic user interface also includes a user input device which a clinician can use for controlling the scanner controller 30 or radiation controller 60 to select scanning sequences or protocols and treatment schemes or doses respectively. The console displays diagnostic images, segmentation tools, the intensity map, surface models, or the like.

Figure 3:
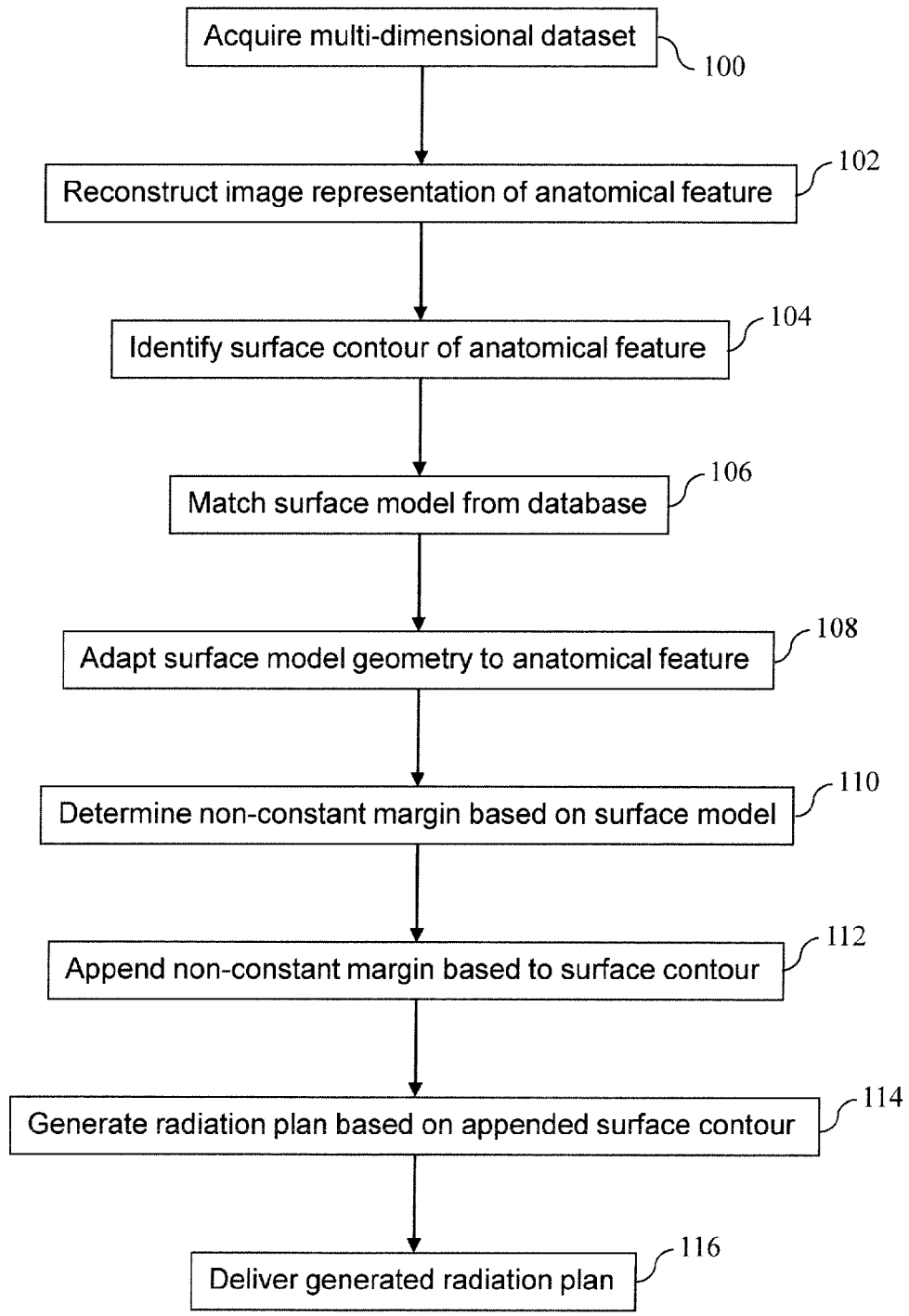
FIG. 3 is a flow chart of a method for image segmentation to determine a non-constant margin.

With reference to FIG. 3, the planning processor 70 includes a processor programmed with a computer program, the computer program being stored on a computer readable medium to perform a method for radiation therapy and a method for image segmentation. The computer readable medium may include optical memory, magnetic memory, or solid state memory such as compact discs (CDs), digital versatile discs (DVDs), flash memory, random access memory (RAM) chips, or the like.

The method for image segmentation and radiation therapy, as depicted in the flowchart, includes acquiring a multi-dimensional data set 100, e.g. image or projection data from a diagnostic image scanner. The data set is reconstructed into an image representation of an anatomical feature which is to be studied 102. A surface contour of the anatomical feature is identified 104. For example, a tumor boundary can be segmented and highlighted. A surface model is matched to the surface contour 106. The matching is based on morphology, position, motion, prior treatment results, functionality of the object of interest, etc. The surface model is fitted to the geometry of the anatomical feature 108. Each surface model has a non-constant margin associated to it. A non-constant margin is determined 110 for the anatomical feature based on the surface model and associated non-constant margin together with other factors, as previously stated. The associated non-constant margin is adjusted or optimized based on the factors which are typically patient specific. The non-constant margin is appended 112 to the surface contour of the anatomical feature and a radiation therapy plan is generated 114 therefrom. The radiation therapy plan is executed and radiation therapy, e.g. gamma radiation, is delivered 116 to the patient anatomy corresponding to the appended surface model.

In another embodiment, follow-up image representations are simulated, e.g. via Monte Carlo methods or the like, using the appended surface model and a statistics describing a probability of deformation and/or functional changes of the anatomical feature. A tumor control probability (TCP) and normal tissue control probability (NTCP) are determined for a plurality of radiation therapy plans generated from the follow-up image representations. The radiation therapy plans are ranked based on a TCP/NTCP ratio, and the best plan is selected.

In another embodiment, the thickness of the margin is uniform for an organ. In normal clinical practice, statistical data and spreading of organ position and functional characteristics are not available or very computational intensive to use. For daily use, the organs are delineated and some regions of interest (ROI) are matched with a predefined model after which these regions are used in the objective functions. The ROI is delineated. The relevant contours of the ROI are matched with a model. The surface of each model has different areas, for each area a distance to the real border and a weight factor is defined. The contours of the surface model are expanded. Objective functions which make use of the organ contours are defined along with the expanded contours with their weight factors. With the collection of plans with (artificial) follow-up images, the distance to the real border and the weight factor per area of the models are determined. The combination of the areas to a single objective function is determined by the organ functional architecture (serial or parallel) and the type of objective function used (biological or physical constraint).

In another embodiment, the planning processor 70 prospectively generates an adaptive radiation therapy plan based on the appended non-constant margin. The CT scanner 12 acquires a planning image of the object of interest and a non-constant margin is determined therefrom by the means for generating a non-constant margin. The planning processor generates a radiation therapy plan according to the appended object of interest. The generated therapy plan includes a plurality of radiation treatment sessions, prior to each session, the CT scanner 12, or other diagnostic imaging modality, acquires a pilot image of the object of interest to align the patient and to monitor the progress of the treatment. The planning processor compares the morphology, position, or the like of the current object of interest to previously determined values, such as from the planning image or previously acquired pilot images. If the difference meets a pre-selected threshold, the non-constant margin is updated according to the current surface contour. In this manner, the planning processor adaptively updates the non-constant margin during the therapy plan. Accordingly, the current treatment session and/or the remaining radiation therapy plan is updated to account for the changes in the appended object of interest. Aspects which are updated include radiation dose, beam trajectory, beam geometry, and/or treatment session schedule; however, other aspects are also contemplated.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

Having thus described the preferred embodiments, the invention is now claimed to be:

1. A method for image segmentation of anatomical features, comprising:
   identifying a surface contour of at least one object of interest from a multi-dimensional data set;
   identifying a surface model based on the surface contour;
   determining a non-constant margin based on the identified surface model and at least one of surface motion and surface morphology of the object of interest, the non-constant margin being appended to the identified surface model;

wherein the surface model includes a plurality of surface regions which define a surface of the surface model, each surface region describes a width and a weight factor of a portion of the non-constant margin corresponding to that surface region.

2. The method according to claim claim 1, wherein the surface model identifying step further includes:
   matching an surface model to the surface contour of the at least one object of interest; and
   adapting a surface of the surface model to correspond to the geometry of the surface contour of the at least one object of interest.

3. The method according to claim 2, wherein matching the surface model to the surface contour of the at least one object of interest is based on at least one of position, morphology, motion, or functionality of the object of interest.

4. A method for radiation therapy, comprising:
   acquiring a multidimensional dataset of a subject;
   reconstructing the multidimensional dataset into at least one image representation of at least one anatomical feature of the subject;
   segmenting the image representation according to the method of claim 1;
   generating a radiation therapy plan according to the segmented image representation, the radiation plan limits the delivery of therapeutic radiation to within the identified surface contour of the anatomical feature and the appended non-constant margin; and
   delivering therapeutic radiation according to the generated radiation therapy plan.

5. A non-transitory computer readable medium carrying a computer program which controls a processor to perform the method of claim 1.

6. An image processing apparatus comprising:
   a segmentation unit which identifies a surface contour of at least one object of interest from a multi-dimensional data set;
   a masking unit which determines a non-constant margin based on the identified surface contour and appends the determined non-constant margin to the identified surface contour;
   an identification unit which identifies a surface model, selected from a surface model database, based on the identified surface contour, wherein the surface model includes a plurality of surface regions which define a surface of the surface model, each surface region describes a width and a weight factor of a portion of the non-constant margin corresponding to that surface region.

7. The method according to claim 1, wherein the non-constant margin is determined based on anisotropic surface motion of the object of interest.

8. The image processing apparatus according to claim 6, wherein the non-constant margin is based on at least one of anisotropic motion, surface morphology, and positional uncertainty.

9. The image processing apparatus according to claim 6, further including:
   a deformation unit which matches the surface model to the surface contour of the at least one object of interest and adapts a surface of the surface model to correspond to the geometry of the surface contour of the at least one object of interest.

10. The image processing apparatus according to claim 9, wherein matching the surface model to the surface contour of the at least one object of interest is based on at least one of position, morphology, motion, or functionality of the object of interest.

11. A radiation therapy system comprising:
    the image processing apparatus according to claim 6;
    an image processor configured to:
    a radiation therapy planning processor configured to generate a radiation therapy plan based on the identified surface contour with the appended non-constant margin for delivery of therapeutic radiation to the object of interest and the surrounding tissue; and
    a radiation delivery system which delivers the therapeutic radiation according to the generated radiation therapy plan.

12. A method for image segmentation of anatomical features, comprising:
    identifying a surface contour of at least one object of interest from a multi-dimensional data set; and
    determining a non-constant margin based on the identified surface contour and at least one of surface motion and surface morphology of the object of interest, the non-constant margin being appended to the identified surface contour;
    wherein the non-constant margin is determined based on anisotropic surface motion of the object of interest;
    wherein the non-constant margin is wider in a direction perpendicular to a direction of the motion than it is in a direction parallel to the direction of the motion.

* * * * *